(12) United States Patent
Newcomb et al.

(10) Patent No.: US 10,573,976 B2
(45) Date of Patent: Feb. 25, 2020

(54) ADHESIVE WITH TAILORABLE ELECTRICAL CONDUCTIVITY FOR MONITORING MECHANICAL PROPERTIES OF ADHESIVE JOINT WITHIN POLYMERIC COMPOSITES

(71) Applicant: GM GLOBAL TECHNOLOGY OPERATIONS LLC, Detroit, MI (US)

(72) Inventors: Bradley A. Newcomb, Troy, MI (US); Xiaosong Huang, Novi, MI (US); Ryan Gergely, Fraser, MI (US); Sean R. Wagner, Shelby Township, MI (US); Chaitanya Sankavaram, Sterling Heights, MI (US); Nicholas P. Irish, Commerce, MI (US); Louis G. Hector, Jr., Shelby Township, MI (US)

(73) Assignee: GM Global Technology Operations LLC, Detroit, MI (US)

(*) Notice: Subject to any disclaimer, the term of this patent is extended or adjusted under 35 U.S.C. 154(b) by 121 days.

(21) Appl. No.: 15/912,618

(22) Filed: Mar. 6, 2018

(65) Prior Publication Data
US 2019/0280397 A1    Sep. 12, 2019

(51) Int. Cl.
| | |
|---|---|
| H01R 4/04 | (2006.01) |
| H05K 3/32 | (2006.01) |
| C09J 9/02 | (2006.01) |
| B32B 7/12 | (2006.01) |
| G01N 27/04 | (2006.01) |

(Continued)

(52) U.S. Cl.
CPC .............. *H01R 4/04* (2013.01); *B32B 7/12* (2013.01); *C09J 5/00* (2013.01); *C09J 9/02* (2013.01); *C09J 11/04* (2013.01); *G01N 27/041* (2013.01); *H05K 3/321* (2013.01); *B32B 2250/02* (2013.01); *B32B 2307/202* (2013.01); *C08K 3/04* (2013.01); *C08K 2201/001* (2013.01)

(58) Field of Classification Search
CPC ...... H01R 4/04; C09J 9/02; C09J 5/00; G01N 27/041; H05K 3/321; B32B 2307/202; B32B 2250/02; B32B 7/12
USPC ........................................... 324/71.1
See application file for complete search history.

(56) References Cited

U.S. PATENT DOCUMENTS

| | | | |
|---|---|---|---|
| 2016/0284449 A1 | 9/2016 | Haq et al. | |
| 2017/0028679 A1* | 2/2017 | Li | B23K 1/20 |
| 2017/0145264 A1 | 5/2017 | Larson | |

OTHER PUBLICATIONS

Roham Mactabi, "In Situ Health Monitoring of Adhesively Bonded Joints during Fatigue Using Carbon Nanotube Network", Concordia University, Montreal, Quebec, Canada, Nov. 2011.
(Continued)

*Primary Examiner* — Farhana A Hoque
(74) *Attorney, Agent, or Firm* — Quinn IP Law (57) ABSTRACT

A functionalized adhesive and systems and methods employing the same are disclosed. The functionalized adhesive is configured to form an adhesive joint between a first substrate and a second substrate. The functionalized adhesive comprises a neat adhesive selected to have a bonding strength above a predetermined bonding threshold and a filler selectively dispersed within the neat adhesive. The filler is selected to modify electrical properties of the neat adhesive such that the functionalized adhesive is electrically conductive with a tailored resistivity and such that a resistance of the adhesive joint is greater than a resistance of the first substrate and the second substrate.

20 Claims, 2 Drawing Sheets

(51) Int. Cl.
*C09J 5/00* (2006.01)
*C09J 11/04* (2006.01)
*C08K 3/04* (2006.01)

(56) References Cited

OTHER PUBLICATIONS

Xoan F. Sanchez-Romate, Maria Sanchez, Carlos Garcia-Nieto, Javier Molinero, Alberto Jiménez-Suárez, Alfredo Güemes and Alejandro Ureña, "Structural Health Monitoring of Bonded Joints Using Carbon Nanotube Doped Adhesive Films", 8th European Workshop on Structural Health Monitoring (EWSHM 2016), Spain, Bilbao, Jul. 5-8, 2016.

J.H. Constable, Thomas Kache, Heiko Teichmann, Sven Muhle, "Continuous Electrical Resistance Monitoring, Pull Strength, and Fatigue Life of Isotropically Conductive Adhesive Joints", State University of New York at Binghamton Binghamton, NY and Michael A. Gaynes IBM Corporation Endicott, NY, Jul. 1999.

* cited by examiner

ADHESIVE WITH TAILORABLE ELECTRICAL CONDUCTIVITY FOR MONITORING MECHANICAL PROPERTIES OF ADHESIVE JOINT WITHIN POLYMERIC COMPOSITES

INTRODUCTION

The disclosure relates to the field of composites and, more specifically, to systems and methods for monitoring mechanical properties of adhesive joints.

Composites include substrates adhered with an adhesive joint therebetween. Passing current between a first electrode on a first substrate and a second electrode on a second substrate does not provide indicia of mechanical properties of the joint. Rather, passing current between the first electrode on the first substrate and the second electrode on the second substrate indicates conditions of the bulk structure—e.g., indicia of the combined mechanical properties of the first substrate, the second substrate, and the adhesive joint—without indicating mechanical properties of the individual components.

Physical alteration to any of the first substrate, the second substrate, and the adhesive joint, such as abrasion of the first substrate, will affect the electrical properties of the composite. Accordingly, a change to a monitoring signal after the physical alteration will not provide an indication as to the nature of the alteration and will not provide an indication of which component or component was altered.

Moreover, because the adhesive joint is generally enclosed by the first substrate and the second substrate, and because the first substrate and the second substrate provide greater exposed areas than the adhesive joint, any change to the electrical properties of the composite are more likely attributable to an alteration of either substrate than to an alteration of the adhesive joint.

SUMMARY

It is desirable to monitor mechanical properties of an adhesive joint between two substrates while inhibiting interfering signals from the substrates. Beneficially, systems and methods according to aspects of the present disclosure may monitor mechanical properties of an adhesive joint by selecting and controlling electrical properties of the adhesive joint in relation to electrical properties of the joined substrates. Beneficially, systems and methods according to aspects of the present disclosure may provide indicia of mechanical properties of the adhesive joint at numerous predetermined portions of the adhesive joint.

According to aspects of the present disclosure, a functionalized adhesive is configured to form an adhesive joint between a first substrate and a second substrate. The functionalized adhesive includes a neat adhesive and a filler. The neat adhesive is selected to have a bonding strength above a predetermined bonding threshold. The filler is selectively dispersed within the neat adhesive. The filler is selected to modify electrical properties of the neat adhesive such that the functionalized adhesive is electrically conductive with a tailored resistivity and such that a resistance of the adhesive joint is greater than a resistance of the first substrate and the second substrate.

According to further aspects of the present disclosure, the tailored resistivity is configured to produce an adhesive joint having a resistance that is at least 10 times higher than the resistance of the first substrate and the second substrate.

According to further aspects of the present disclosure, the filler is a functionalized filler that includes a filler substrate and a functional polymer extending therefrom. The filler substrate is a carbon nanostructure, and the functional polymer is grafted to the carbon nanostructure.

According to further aspects of the present disclosure, the filler is a functionalized filler that includes a filler substrate and a functional polymer extending therefrom, and the functional polymer is an electrically conductive polymer.

According to further aspects of the present disclosure, the filler is a functionalized filler that includes a filler substrate and a functional polymer extending therefrom. The functional polymer is electrically non-conductive, and the functional polymer is selected to increase interaction between the functionalized filler and the neat adhesive.

According to further aspects of the present disclosure, the filler includes a plurality of first components having a first aspect ratio and a plurality of second components having a second aspect ratio, and a difference between the first aspect ratio and the second aspect ratio is selected to provide the tailored resistivity.

According to aspects of the present disclosure, a composite structure includes a first substrate, a second substrate, an adhesive joint, an electrode array. The first substrate and the second substrate have a substrate resistivity. The adhesive joint attaches the first substrate to the second substrate. The adhesive joint includes a functionalized adhesive consisting of a neat adhesive and a filler. The neat adhesive is selected to have a bonding strength above a predetermined bonding threshold. The filler is selectively dispersed within the neat adhesive. The filler is selected to modify electrical properties of the neat adhesive such that the functionalized adhesive is electrically conductive with a tailored resistivity and such that a resistance of the adhesive joint is greater than the substrate resistivity. The electrode array is configured to monitor mechanical properties of the adhesive joint. The electrode array includes a first electrode electrically coupled to the adhesive joint via the first substrate and a second electrode electrically coupled to the adhesive joint via the second substrate. The first electrode and the second electrode are positioned such that measurement of a resistance experienced by a current passed between the first electrode and the second electrode provides indicia of mechanical properties of the adhesive joint and inhibits indicia of mechanical properties of the first substrate and the second substrate.

According to further aspects of the present disclosure, the filler is a functionalized filler that includes a filler substrate and a functional polymer extending therefrom. The filler substrate is a carbon nanostructure, and the functional polymer is grafted to the carbon nanostructure.

According to further aspects of the present disclosure, the filler is a functionalized filler includes a filler substrate and a functional polymer extending therefrom, and the functional polymer is an electrically conductive polymer.

According to further aspects of the present disclosure, the functionalized filler further includes a second functional polymer extending from the filler substrate. The second functional polymer is a non-conductive polymer configured to modify a viscosity of the functionalized adhesive, a mechanical property of the adhesive joint, a thermal property of the functionalized adhesive, or a combination thereof.

According to further aspects of the present disclosure, the electrode array further includes a third electrode electrically coupled to the adhesive joint via the second substrate, indicia provided by measurement of the resistance experienced by the current passed between the first electrode and the second electrode indicate mechanical properties at a first predetermined portion of the adhesive joint, indicia provided by measurement of a second resistance experienced by a second current passed between the first electrode and the third electrode indicate mechanical properties at a second predetermined portion of the adhesive joint, and the first predetermined portion is distinct from the second predetermined portion.

According to further aspects of the present disclosure, the electrode array further includes a third electrode electrically coupled to the adhesive joint via the second substrate and a fourth electrode electrically coupled to the adhesive joint via the first substrate, indicia provided by measurement of the resistance experienced by the current passed between the first electrode and the second electrode indicate mechanical properties at a first predetermined portion of the adhesive joint, indicia provided by measurement of a second resistance experienced by a second current passed between the third electrode and the fourth electrode indicate mechanical properties at a second predetermined portion of the adhesive joint, and the first predetermined portion is distinct from the second predetermined portion.

According to further aspects of the present disclosure, the electrode array further includes a plurality of sets of electrodes, and measured resistances of currents passed between each respective set of electrodes provides a 3-D model of mechanical properties of the adhesive joint.

According to aspects of the present disclosure, a method includes attaching a first substrate to a second substrate using an adhesive joint and monitoring mechanical properties of the adhesive joint via an electrode array. The first substrate and the second substrate have a substrate resistance. The adhesive joint includes a functionalized adhesive consisting of neat adhesive and a filler selectively dispersed within the neat adhesive. The neat adhesive is selected to have a bonding strength above a predetermined bonding threshold. The filler is selected to modify electrical properties of the neat adhesive such that the functionalized adhesive is electrically conductive with a tailored resistivity. The tailored resistivity provides a resistance of the adhesive joint that is greater than the substrate resistance. The electrode array includes a first electrode electrically coupled to the adhesive joint via the first substrate and a second electrode electrically coupled to the adhesive joint via the second substrate. Monitoring the mechanical properties of the adhesive joint includes passing a current between the first electrode and the second electrode, measuring a resistance experienced by the current between the first electrode and the second electrode, and determining, in response to measuring the resistance, mechanical properties of the adhesive joint using the tailored resistivity.

According to further aspects of the present disclosure, the resistance of the adhesive joint is at least 10 times greater than the substrate resistance.

According to further aspects of the present disclosure, the resistance of the adhesive joint is at least 100 times greater than the substrate resistance.

According to further aspects of the present disclosure, the filler is a functionalized filler includes a filler substrate and a functional polymer extending therefrom, and the functional polymer being grafted on the filler substrate includes treating the filler substrate to produce a precursor particle having a plurality of active groups on a surface thereof, exposing the precursor particle to a monomer solution to thereby produce the functional polymer extending from the active groups on the surface of the filler substrate, and inhibiting, in response to reaching a desired chain length of the functional polymer, polymerization of the functional polymer to thereby produce the functionalized filler.

According to further aspects of the present disclosure, the filler is a functionalized filler includes a filler substrate, a first functional polymer, and a second functional polymer. The first functional polymer and the second functional polymer extend from the filler substrate. The first functional polymer is a conductive polymer and the second functional polymer is a non-conductive polymer. The first functional polymer is configured to provide the tailored resistivity. The second functional polymer is configured to modify a viscosity of the functionalized adhesive, a mechanical property of the adhesive joint, a thermal property of the functionalized adhesive, or combinations thereof.

According to further aspects of the present disclosure, the electrode array further includes a third electrode electrically coupled to the adhesive joint via the second substrate, indicia provided by measurement of the resistance experienced by the current passed between the first electrode and the second electrode indicate mechanical properties at a first predetermined portion of the adhesive joint, indicia provided by measurement of a second resistance experienced by a second current passed between the first electrode and the third electrode indicate mechanical properties at a second predetermined portion of the adhesive joint, and the first predetermined portion is distinct from the second predetermined portion, and monitoring mechanical properties of the adhesive joint further includes passing the second current between the first electrode and the third electrode, measuring the second resistance experienced by the second current between the first electrode and the third electrode, and determining, in response to measuring the second resistance, mechanical properties of the adhesive joint at the second predetermined portion using the tailored resistivity.

According to further aspects of the present disclosure, the electrode array further includes a third electrode electrically coupled to the adhesive joint via the second substrate and a fourth electrode electrically coupled to the adhesive joint via the first substrate, indicia provided by measurement of the resistance experienced by the current passed between the first electrode and the second electrode indicate mechanical properties at a first predetermined portion of the adhesive joint, indicia provided by measurement of a second resistance experienced by a second current passed between the third electrode and the fourth electrode indicate mechanical properties at a second predetermined portion of the adhesive joint, the first predetermined portion is distinct from the second predetermined portion, and monitoring mechanical properties of the adhesive joint further includes passing the second current between the third electrode and the fourth electrode, measuring the second resistance experienced by the second current between the first electrode and the third electrode, and determining, in response to measuring the second resistance, mechanical properties of the adhesive joint at the second predetermined portion using the tailored resistivity.

The above features and advantages and other features and advantages of the present disclosure are readily apparent from the following detailed description of the best modes for carrying out the disclosure when taken in connection with the accompanying drawings.

BRIEF DESCRIPTION OF THE DRAWINGS

The drawings are illustrative and not intended to limit the subject matter defined by the claims. Exemplary aspects are discussed in the following detailed description and shown in the accompanying drawings in which:

DETAILED DESCRIPTION

Systems and methods according to the present disclosure provide for monitoring mechanical properties of an adhesive joint between two substrates. In some aspects, the monitored mechanical properties may include at least one of an adhesive stress or strain profile, adhesive cracking, plastic deformation of the adhesive, adhesive debonding from the substrate, combinations thereof, and the like.

Beneficially, systems and methods described herein may be used to tailor electrical properties of a functionalized adhesive within an adhesive joint between joined substrates to provide indicia of mechanical properties of the adhesive joint while inhibiting interfering indicia of mechanical properties or alterations to the joined substrates. What is more, interfering indicia of mechanical properties or alterations to the joined substrates are inhibited without the need for electrodes disposed directly on surfaces of the adhesive joint or within the adhesive joint.

Further, systems and methods described herein beneficially provide for selection of a neat adhesive based on adhesive and mechanical properties provided by the neat adhesive after curing while providing for effective indication of mechanical properties of the adhesive joint using electrical monitoring.

Yet further, systems and methods described herein beneficially provide for monitoring of joint health at individual portions of the adhesive joint, for example, to produce 2-D or 3-D profiles spatially describing the mechanical properties within the adhesive joint.

Figure 1:
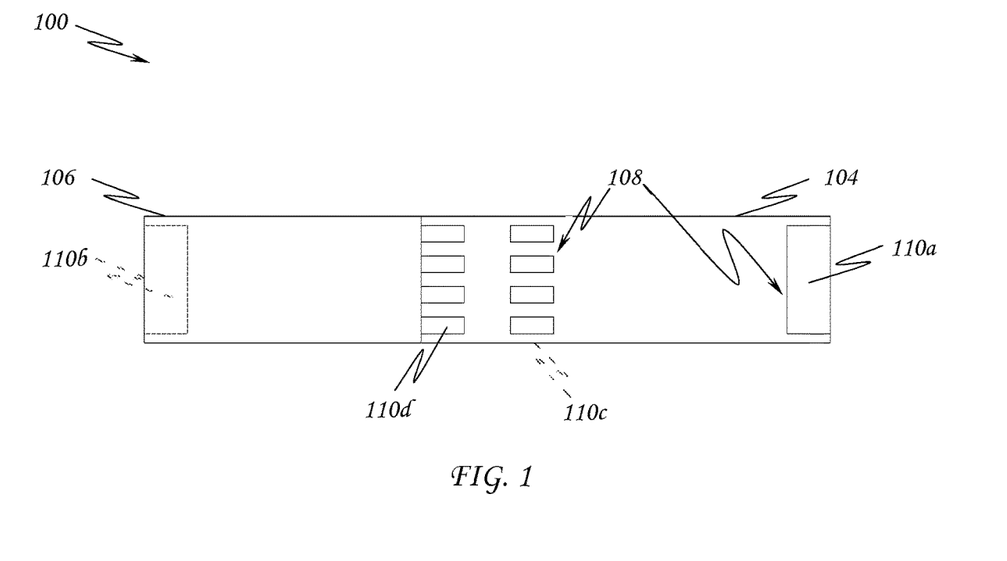
FIG. 1 is a schematic plan view of a system for monitoring mechanical properties of an adhesive joint, according to aspects of the present disclosure.
Figure 2:
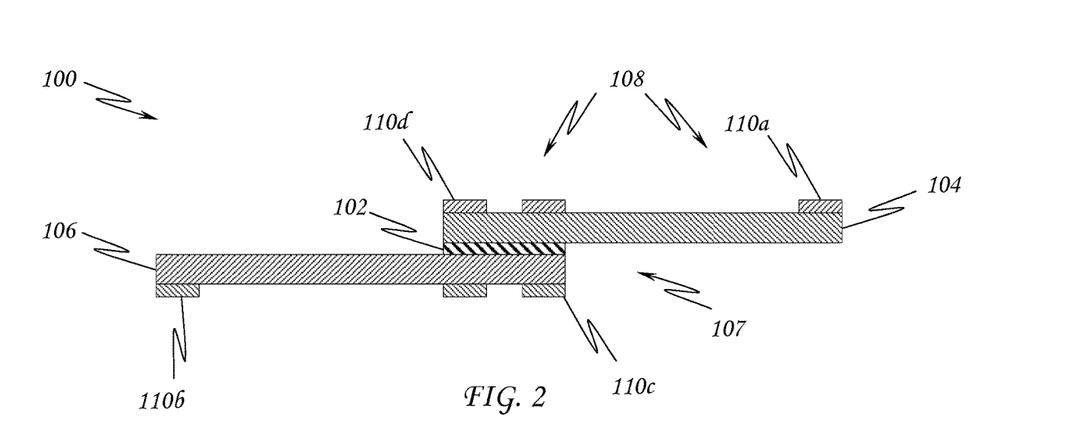
FIG. 2 is a schematic cross-sectional view of the system of FIG. 1, according to aspects of the present disclosure.

Referring now to FIGS. 1 and 2, a system 100 for monitoring mechanical properties of an adhesive joint 102 is shown. The system 100 includes a first substrate 104, a second substrate 106, an adhesive joint 102 therebetween to form a composite structure 107, and an electrode array 108 to pass monitoring signals between the first substrate 104 and the second substrate 106 via the adhesive joint 102.

The first substrate 104 and the second substrate 106 can be formed from any desired materials to produce a structure having desired mechanical properties. The first substrate 104 and the second substrate 106 may be, for example, metals, non-metals, polymers, composites, combinations thereof, and the like. The first substrate 104 and the second substrate 106 may be formed from the same material or different materials. The first substrate 104 and the second substrate 106 have a substrate resistivity which changes depending on the material or materials selected to form the substrates.

The adhesive joint 102 attaches the first substrate 104 to the second substrate 106. The adhesive joint 102 includes a functionalized adhesive. The functionalized adhesive consists of a neat adhesive and a filler.

The neat adhesive is selected to form a polymer matrix with a bonding strength above a predetermined bonding threshold. The first substrate 104, the second substrate 106, and the neat adhesive may be selected to produce a composite structure 107 having desired mechanical properties.

The filler is selectively dispersed within the neat adhesive. The functionalized adhesive is loaded with the filler to at least the percolation threshold to provide the functionalized adhesive with the tailored resistivity. The filler is selected to modify electrical properties of the neat adhesive such that the functionalized adhesive is electrically conductive with a tailored resistivity. The tailored resistivity is greater than the substrate resistivity. In some aspects, the filler includes at least one of carbon particulates, carbon nanotubes, carbon nanofibers, carbon nanowires, and carbon nanoplatelets, carbon black, copper components, silver components, combinations thereof, and the like.

Beneficially, the tailored resistivity of the functionalized adhesive is selected such that resistance of the resulting adhesive joint 102 indicated by a monitoring signal is greater than the resistance of the substrates (e.g., the first substrate 104 and the second substrate 106) indicated by the monitoring signal. In some aspects, the resistance of the adhesive joint 102 is at least an order of magnitude (e.g., about 10 times) greater than the substrate resistance. Surprisingly, this resistance difference isolates the monitoring signals to carrying indicia of mechanical properties of the adhesive joint 102 while inhibiting interference from indicia of mechanical properties of the substrates. In some aspects, the resistance of the adhesive joint 102 is at least two orders of magnitude (e.g., about 100 times) greater than the substrate resistivity. Surprisingly, this resistance difference substantially isolates the monitoring signals to carrying indicia of mechanical properties of the adhesive joint 102 while substantially inhibiting interference from indicia of mechanical properties of the substrates. In some aspects, the resistance of the adhesive joint 102 is at least several orders of magnitude (e.g., at least about 1000 times) greater than the substrate resistance. Surprisingly, this resistance difference substantially isolates the monitoring signals to carrying indicia of mechanical properties of the adhesive joint 102 while preventing interference from indicia of mechanical properties of the substrates.

In some aspects, the filler is a functionalized filler. The functionalized filler includes a plurality of filler substrates with at least one functional polymer extending from each of the filler substrates. The functional polymers extending from each of the filler substrates include a molecular chain with a first end coupled to the filler substrate and a second end distal to the filler substrate. The filler substrate may be electrically conductive or electrically non-conductive. For example, the filler substrate may be at least one of carbon nanostructures, carbon black, copper components, silver components, combinations thereof, and the like.

The functional polymer is selected to modify electrical properties of the filler substrate. The functional polymer may be electrically conductive or electrically non-conductive. In some aspects, the filler substrate is electrically conductive and the functional polymer is either electrically conductive or electrically non-conductive. In some aspects, the filler substrate is electrically non-conductive and the functional polymer is electrically conductive.

In some aspects, the filler substrate is modified using only one functional polymer. In some examples, the filler substrate is a carbon nanostructure and the functional polymer is an electrically conductive polymer grafted thereto. In some examples, the filler substrate is a carbon particulate, carbon nanotube, carbon nanofiber, carbon nanowire, o carbon nanoplatelet and the functional polymer is an electrically non-conductive polymer such as methacrylate.

Examples of carbon nanostructures include carbon nanotubes, carbon nanofibers, carbon nanowires, and carbon nanoplatelets. Examples of electrically conductive polymers include polypyrrole, polythiophene, poly(acetylene), and polyaniline.

In some aspects, the filler substrate is modified using multiple functional polymers. For example, the filler substrate may be modified with a first functional polymer to provide the tailored resistivity of the functional adhesive and a second functional polymer to provide other properties of the functionalized adhesive. In some aspects, the other properties may be a tailored viscosity of the functionalized adhesive, a tailored interaction with the neat adhesive, a tailored strength of the adhesive joint 102, or a tailored thermal property of the functionalized adhesive.

In some aspects, the filler includes a blend of components having different aspect ratios to tailor electrical properties of the functionalized adhesive. The filler may include a plurality of first components having a first aspect ratio and a plurality of second components having a second aspect ratio. The plurality of first components and the plurality of second components may be the same chemical composition, such as pure carbon. The first aspect ratio provides the first component with a first electrical resistivity while the second aspect ratio provides the second component with a second electrical resistivity. The amount of the first component and the amount of the second component are selected such that the desired electrical properties of the functionalized adhesive are achieved. In some embodiments, the filler includes a blend of two or more carbon forms selected from the group consisting of carbon particulates, carbon nanotubes, carbon nanofibers, carbon nanowires, and carbon nanoplatelets.

In some aspects, the filler is a functionalized polymer disposed within the polymer matrix. In some aspects, the functionalized polymer is chemically bonded to the polymer matrix. For example, the polymer matrix and functional polymer may include sites to provide crosslinking between the functionalized polymer and polymer matrix. In some aspects, the functionalized polymer is physically entrapped by the polymer matrix. For example, the functionalized polymer may include a molecular chain length that is long enough to inhibit diffusion of the functionalized polymer through the polymer matrix.

Beneficially, because of the ability to tailor properties of the functionalized adhesive, the first substrate 104 and the second substrate 106 may be selected for desirable mechanical properties without regard to conductivity or resistivity of the substrates. Rather, according to aspects of the present disclosure, electrical properties of the adhesive joint 102 are modified and tailored based on the selected substrates to overcome electrical properties of the selected substrate materials. Further, if either of the first substrate 104 and the second substrate 106 are non-conductive materials, then the respective substrate may be modified to provide electrical conduction between electrodes disposed thereon and the adhesive joint 102.

The electrode array 108 includes at least one set of electrodes 110a-d disposed at predetermined locations on the first substrate 104 and the second substrate 106. Each set of electrodes 110a-d within the electrode array 108 is configured to pass a current through a predetermined portion of the adhesive joint 102. Measurement of electrical properties of the current passing through the adhesive joint 102, such as sensing a voltage drop or measuring a resistance experienced, is used to provide indicia of mechanical properties of the adhesive joint 102.

The electrical properties of the current passing through the adhesive joint 102 may be determined. In some aspects, the electrical properties are determined by calculating values using a sensed measurement or referencing values in a lookup table corresponding to a sensed measurement. In some aspects, the electrical properties are determined by directly sensing a desired property such as a voltage drop across the predetermined portion of the adhesive joint 102.

In some aspects, a voltage drop across the predetermined portion of the adhesive joint 102 is sensed using techniques such as a two-probe measurement or a four-probe measurement. In the two-probe measurement, a single set of electrodes 110a-d provides the current through the adhesive joint 102 and senses the voltage drop across the adhesive joint 102. In the four-probe measurement, a first set of electrodes 110a-d provides the current through the adhesive joint 102 and a second set of electrodes 110a-d senses the voltage drop across the adhesive joint 102. In some aspects, the second set of electrodes 110a-d is configured to sense the voltage drop across the adhesive joint 102 during a first measurement and provide the current through the adhesive joint 102 during a second measurement. In some aspects, the second set of electrodes 110a-d is dedicated to sensing the voltage drop across the adhesive joint 102. Beneficially, using the second set of electrodes 110a-d for dedicated sensing may provide for more sensitive measurement of a voltage drop across the adhesive joint 102 because the second set of electrodes does not have to handle the entire current being passed therethrough. The sensed voltage drop can be used as a measurement of resistance experienced by the current.

In some aspects, the electrode array 108 consists of a single set of electrodes 110a-d and the received indicia indicate mechanical properties representative of the adhesive joint 102. Beneficially, the single set of electrodes 110a-d can be positioned to provide indicia of mechanical properties of the adhesive joint 102 at a position that is likely to be altered during a life of the composite structure 107.

In some aspects, the electrode array 108 includes multiple sets of electrodes 110a-d, and the indicia received by each set of electrodes 110a-d indicate mechanical properties representative of a respective portion of the adhesive joint 102. Beneficially, the multiple sets of electrodes 110a-d can be positioned to provide indicia of mechanical properties of the adhesive joint 102 at a number of predetermined portions of the adhesive joint 102. For example, according to aspects of the present disclosure, passing current between a first set of electrodes 110a-d within the electrode array 108 provides indicia of mechanical properties of a first predetermined portion of the joint, and passing current between a second set of electrodes 110a-d within the electrode array 108 provides indicia of mechanical properties of a second predetermined portion of the joint. In some aspects, the first set of electrodes includes a first electrode 110a and a second electrode 110b, and the second set of electrodes includes a third electrode 110c and a fourth electrode 110d. In some aspects, the first set of electrodes includes a first electrode 110a and a second electrode 110b, and the second set of electrodes includes the first electrode 110a and a third electrode 110c. In some aspects, a first set of electrodes includes the first electrode 110a and the second electrode 110b, a second set of electrodes includes the first electrode 110a and the third electrode 110c, and a third set of electrodes includes the third electrode 110c and the fourth electrode 110d. Beneficially, according to aspects of the present disclosure, the electrode array 108 can be used to provide a 3-D map of mechanical properties of the adhesive joint 102 from the indicia received using multiple sets of electrodes 110a-d.

The predetermined locations of the electrodes 110a-d may be proximal to or distal from the adhesive joint. Beneficially, according to aspects of the present disclosure, traces, via holes, or substrate doping may be used to decrease the substrate resistance experienced by the current passed between respective sets of electrodes 110a-d. The traces may extend along either a portion of or all of the first substrate 104 and the second substrate 106. The via holes may extend through either a portion of or all of the first substrate 104 and the second substrate 106 The substrate doping may include doping the first substrate 104 and/or the second substrate 106 with conductive particles, such as carbon black, at predetermined locations. These predetermined locations are disposed between the electrodes 110a-d and the adhesive joint 102 to conduct current therebetween.

Figure 3:
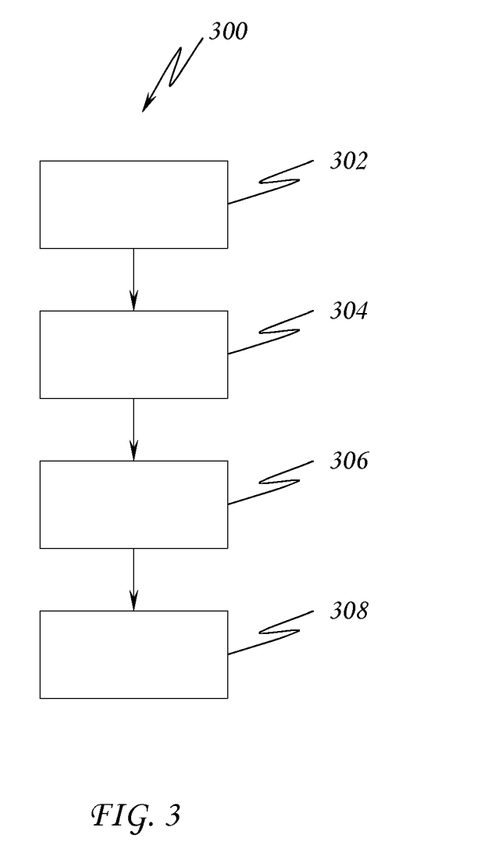
FIG. 3 is a flowchart of a method of monitoring mechanical properties of an adhesive joint.

Referring now to FIG. 3, a method 300 for monitoring mechanical properties of an adhesive joint 102 is shown. The mechanical properties include, for example, strain exerted on the adhesive joint 102. The method 300 includes attaching 302 the first substrate 104 to the second substrate 106 using the adhesive joint 102 and monitoring 304 mechanical properties of the adhesive joint 102 via the electrode array 108. The monitoring 304 includes passing a current between the first electrode 110a and the second electrode 110b, measuring 306 the resistance associated with the current between the first electrode 110a and the second electrode 110b, and determining 308, in response to measuring 306 the resistance, the indicia of mechanical properties of the adhesive joint 102.

Figure 4:
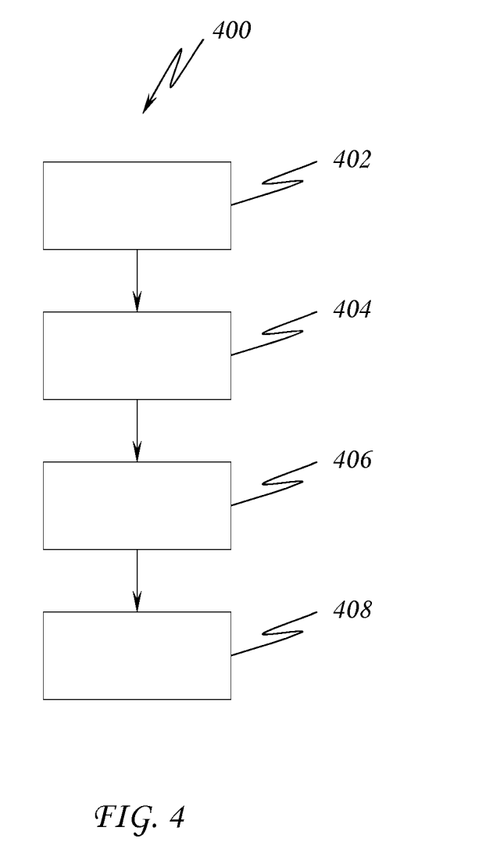
FIG. 4 is a flowchart of a method of grafting at least one functional polymer onto a filler substrate.

Referring now to FIG. 4, a method 400 for grafting the at least one functional polymer onto the filler substrate is shown. In some aspects, the method 400 includes selecting 402 a filler substrate, treating 404 the filler substrate to produce a precursor particle having a plurality of active groups on a surface thereof, exposing 406 the precursor particle to a monomer solution to thereby produce a plurality of functional polymers extending from the active groups on the surface of the filler substrate, and inhibiting 408 polymerization of the at least one functional polymer when a desired molecular chain length has been attained to thereby produce the functionalized particles.

While not being bound by theory, it is believed that viscosity of the functionalized adhesive increases as chain length of the functionalized polymer increases. Further, while not being bound by theory, for filler substrates that are more conductive than the functionalized polymer, increasing chain length will decrease resistivity of the resulting adhesive joint 102. What is more, while not being bound by theory, for neat adhesives that have a greater affinity for the functionalized polymer than the filler substrate, increasing chain length will increase mechanical properties of the resulting adhesive joint 102. Beneficially, such increases, if undesired, may be reduced by reducing grafting density.

In some aspects, the precursor particle may include a first plurality of active groups and a second plurality of active groups. The first plurality of active groups is configured to initiate polymerization of the first functional polymer when exposed to a first monomer solution, and the second plurality of active groups is configured to initiate polymerization of the second functional polymer when exposed to a second monomer solution. In some aspects, the precursor particle is exposed to the first monomer solution and the second monomer solution simultaneously.

While the best modes for carrying out the disclosure have been described in detail, those familiar with the art to which this disclosure relates will recognize various alternative designs and embodiments for practicing the disclosure within the scope of the appended claims.

What is claimed is:

1. A functionalized adhesive configured to form an adhesive joint between a first substrate and a second substrate, the functionalized adhesive comprising:
   a neat adhesive selected to have a bonding strength above a predetermined bonding threshold; and
   a filler selectively dispersed within the neat adhesive, the filler selected to modify electrical properties of the neat adhesive such that the functionalized adhesive is electrically conductive with a tailored resistivity and such that a resistance of the adhesive joint is greater than a resistance of the first substrate and the second substrate;
   wherein the filler is a functionalized filler including:
      a filler substrate; and
      a functional polymer extending from the filler substrate and including a molecular chain with a first end coupled to the filler substrate and a second end distal to the filler substrate.

2. The functionalized adhesive of claim 1, wherein the tailored resistivity is configured to produce an adhesive joint having a resistance that is at least 10 times higher than the resistance of the first substrate and the second substrate.

3. The functionalized adhesive of claim 1, wherein the filler substrate is a carbon nanostructure, and the functional polymer is grafted to the carbon nanostructure.

4. The functionalized adhesive of claim 1, wherein the functional polymer is an electrically conductive polymer.

5. The functionalized adhesive of claim 1, wherein the functional polymer is electrically non-conductive, and the functional polymer is selected to increase interaction between the functionalized filler and the neat adhesive.

6. The functionalized adhesive of claim 1, wherein the filler includes a plurality of first components having a first aspect ratio and a plurality of second components having a second aspect ratio, and wherein a difference between the first aspect ratio and the second aspect ratio is selected to provide the tailored resistivity.

7. A composite structure comprising:
   a first substrate and a second substrate having a substrate resistivity;
   an adhesive joint attaching the first substrate to the second substrate, the adhesive joint including a functionalized adhesive consisting of:
      a neat adhesive selected to have a bonding strength above a predetermined bonding threshold; and
      a filler selectively dispersed within the neat adhesive, the filler selected to modify electrical properties of the neat adhesive such that the functionalized adhesive is electrically conductive with a tailored resistivity and such that a resistance of the adhesive joint is greater than the substrate resistivity; and
   an electrode array configured to monitor mechanical properties of the adhesive joint, the electrode array including:
      a first electrode electrically coupled to the adhesive joint via the first substrate, and
      a second electrode electrically coupled to the adhesive joint via the second substrate, the first electrode and the second electrode being positioned such that measurement of a resistance experienced by a current passed between the first electrode and the second electrode provides indicia of mechanical properties of the adhesive joint and inhibits indicia of mechanical properties of the first substrate and the second substrate.

8. The composite structure of claim 7, wherein the filler is a functionalized filler including a filler substrate and a functional polymer extending therefrom, the filler substrate is a carbon nanostructure, and the functional polymer is grafted to the carbon nanostructure.

9. The composite structure of claim 7, wherein the filler is a functionalized filler including a filler substrate and a functional polymer extending therefrom, and the functional polymer is an electrically conductive polymer.

10. The composite structure of claim 9, wherein the functionalized filler further includes a second functional polymer extending from the filler substrate, the second functional polymer is a non-conductive polymer configured to modify a viscosity of the functionalized adhesive, a mechanical property of the adhesive joint, a thermal property of the functionalized adhesive, or a combination thereof.

11. The composite structure of claim 7, wherein the electrode array further comprises a third electrode electrically coupled to the adhesive joint via the second substrate, wherein indicia provided by measurement of the resistance experienced by the current passed between the first electrode and the second electrode indicate mechanical properties at a first predetermined portion of the adhesive joint, wherein indicia provided by measurement of a second resistance experienced by a second current passed between the first electrode and the third electrode indicate mechanical properties at a second predetermined portion of the adhesive joint, and wherein the first predetermined portion is distinct from the second predetermined portion.

12. The composite structure of claim 7, wherein the electrode array further comprises a third electrode electrically coupled to the adhesive joint via the second substrate and a fourth electrode electrically coupled to the adhesive joint via the first substrate, wherein indicia provided by measurement of the resistance experienced by the current passed between the first electrode and the second electrode indicate mechanical properties at a first predetermined portion of the adhesive joint, wherein indicia provided by measurement of a second resistance experienced by a second current passed between the third electrode and the fourth electrode indicate mechanical properties at a second predetermined portion of the adhesive joint, and wherein the first predetermined portion is distinct from the second predetermined portion.

13. The composite structure of claim 7, wherein the electrode array further includes a plurality of sets of electrodes, and wherein measured resistances of currents passed between each respective set of electrodes provides a 3-D model of mechanical properties of the adhesive joint.

14. A method comprising:
attaching a first substrate to a second substrate using an adhesive joint, the first substrate and the second substrate having a substrate resistance, the adhesive joint including a functionalized adhesive consisting of neat adhesive and a filler selectively dispersed within the neat adhesive, the neat adhesive selected to have a bonding strength above a predetermined bonding threshold, the filler selected to modify electrical properties of the neat adhesive such that the functionalized adhesive is electrically conductive with a tailored resistivity, the tailored resistivity providing a resistance of the adhesive joint that is greater than the substrate resistance; and
monitoring mechanical properties of the adhesive joint via an electrode array, the electrode array including a first electrode electrically coupled to the adhesive joint via the first substrate and a second electrode electrically coupled to the adhesive joint via the second substrate, wherein monitoring mechanical properties of the adhesive joint includes:
passing a current between the first electrode and the second electrode,
measuring a resistance experienced by the current between the first electrode and the second electrode, and
determining, in response to measuring the resistance, mechanical properties of the adhesive joint using the tailored resistivity.

15. The method of claim 14, wherein the resistance of the adhesive joint is at least 10 times greater than the substrate resistance.

16. The method of claim 14, wherein the resistance of the adhesive joint is at least 100 times greater than the substrate resistance.

17. The method of claim 14, wherein the filler is a functionalized filler including a filler substrate and a functional polymer extending therefrom, the functional polymer being grafted on the filler substrate including:
treating the filler substrate to produce a precursor particle having a plurality of active groups on a surface thereof;
exposing the precursor particle to a monomer solution to thereby produce the functional polymer extending from the active groups on the surface of the filler substrate; and
inhibiting, in response to reaching a desired chain length of the functional polymer, polymerization of the functional polymer to thereby produce the functionalized filler.

18. The method of claim 14, wherein the filler is a functionalized filler including a filler substrate, a first functional polymer, and a second functional polymer, the first functional polymer and the second functional polymer extending from the filler substrate, wherein the first functional polymer is a conductive polymer and the second functional polymer is a non-conductive polymer, the first functional polymer configured to provide the tailored resistivity, the second functional polymer configured to modify a viscosity of the functionalized adhesive, a mechanical property of the adhesive joint, a thermal property of the functionalized adhesive, or combinations thereof.

19. The method of claim 14, wherein the electrode array further comprises a third electrode electrically coupled to the adhesive joint via the second substrate, wherein indicia provided by measurement of the resistance experienced by the current passed between the first electrode and the second electrode indicate mechanical properties at a first predetermined portion of the adhesive joint, wherein indicia provided by measurement of a second resistance experienced by a second current passed between the first electrode and the third electrode indicate mechanical properties at a second predetermined portion of the adhesive joint, and wherein the first predetermined portion is distinct from the second predetermined portion, and wherein monitoring mechanical properties of the adhesive joint further includes:
passing the second current between the first electrode and the third electrode,
measuring the second resistance experienced by the second current between the first electrode and the third electrode, and
determining, in response to measuring the second resistance, mechanical properties of the adhesive joint at the second predetermined portion using the tailored resistivity.

20. The method of claim 14, wherein the electrode array further comprises a third electrode electrically coupled to the adhesive joint via the second substrate and a fourth electrode electrically coupled to the adhesive joint via the first substrate, wherein indicia provided by measurement of the resistance experienced by the current passed between the first electrode and the second electrode indicate mechanical properties at a first predetermined portion of the adhesive joint, wherein indicia provided by measurement of a second resistance experienced by a second current passed between the third electrode and the fourth electrode indicate mechanical properties at a second predetermined portion of the adhesive joint, wherein the first predetermined portion is distinct from the second predetermined portion, and wherein monitoring mechanical properties of the adhesive joint further includes:

- passing the second current between the third electrode and the fourth electrode,
- measuring the second resistance experienced by the second current between the first electrode and the third electrode, and
- determining, in response to measuring the second resistance, mechanical properties of the adhesive joint at the second predetermined portion using the tailored resistivity.

\* \* \* \* \*